United States Patent [19]
Young

[11] Patent Number: 4,963,167
[45] Date of Patent: Oct. 16, 1990

[54] AIR DELIVERY MONITORING SYSTEMS

[76] Inventor: Peter S. Young, 9690 Calle La Cuesta, Riverside, Calif. 92503

[21] Appl. No.: 438,185

[22] Filed: Nov. 20, 1989

[51] Int. Cl.⁵ ............................................. B01D 46/00
[52] U.S. Cl. ........................................ 55/97; 55/270;
  55/481; 73/863.23; 73/863.25; 73/863.81
[58] Field of Search ........................... 55/270, 97, 481;
  73/863.25, 863.81, 863.23; 98/2.11, 40.1

[56] References Cited

U.S. PATENT DOCUMENTS

| | | | |
|---|---|---|---|
| 2,057,568 | 10/1936 | Gerard | 55/481 |
| 2,575,499 | 11/1951 | Manow | 55/481 |
| 3,010,583 | 11/1961 | Kenyon | 73/863.23 |
| 4,544,386 | 10/1985 | Trayford et al. | 55/270 |

Primary Examiner—Bernard Nozick

[57] ABSTRACT

An air delievery monitoring system covers an aperture of an air duct with an insert having a bore. A filter element in communication with the inside of that air duct through that bore is made accessible from outside of that duct. Air escapes from the duct through the bore in the insert to the filter element which traps contaminants in such air for subsequent laboratory analysis. The filter element is preferably encapsulated in an apertured filter element housing which is mounted in the insert in communication with its bore. After removal of that housing from the insert, the contaminated filter element can be transported or sent to the laboratory for the performance of several analyses thereon.

20 Claims, 1 Drawing Sheet

AIR DELIVERY MONITORING SYSTEMS

BACKGROUND OF THE INVENTION

1. Field of the Invention

The subject invention relates to monitoring systems and, more specifically, to methods and apparatus for monitoring air delivery systems, including air conditioning and heating systems, and relates also to systems for assuring the quality of inside air in buildings and other structures.

2. Information Disclosure Statement

The following comments are offered by way of background.

Dirty air systems cause or are associated with many problems such as:

High employee absenteeism and loss of productivity due to colds, flue, itchy eyes, skin rashes, respiratory problems, and the like, all the way to serious illnesses such as legionella, pathogenic virus, and more.

Fungus growing in ductwork can corrode microcomponents and metal surfaces on delicate instruments, crash computer heads, cause failures in electronic phone equipment, contaminate laboratory work, and more,

- Become a serious fire hazard. Particularly when fire dampers and other mechanisms within the system malfunction,
- Create unsightly grilles and diffusers, ceiling tiles, generally dirty appearance, requiring costly maintenance,
- Cause rapid deterioration of soft furnishings such as drapes, carpet and upholstery,
- Increase energy costs due to lower performance levels, and/or
- Create air flow problems such as lack of air, hot or cold spots and make it impossible to balance a system properly or achieve proper temperature, and decrease equipment life and increase related maintenance problems.

The need for a clean system has become obvious to most building owners and managers in recent years. What has NOT become obvious is how to do it!

Some contractors have made a good living from the fact that most people cannot visually inspect their ductwork. Major cleaning contracts have been awarded solely on the fact of dirty grilles and diffusers. Unanswered questions such as the following can be costly and dangerous:

- How much of the visible dirt is due to a venturi effect, and not dirty ducting?
- Could some areas be dirty while others are clean, yet you paid for cleaning the entire system?
- Has cause and effect been established so the customer can be guaranteed that cleaning of the system will accomplish the desired goals?
- Are the ducts truly clean or is the bacteria level still unacceptable for the building's environment?
- Have pre/post conditions and findings been documented so the customer has proof and a permanent management tool?

In an effort to counter these problems chunks of contaminants have been removed from duct work and have been subjected to analyses for asbestos, fiberglass, rust, particulate content, etc. In practice, however, such a procedure was complicated and difficult to perform and to implement on a regular basis.

In a different vein, methods and means for microorganism analysis have been known for a long time, as may, for instance, be seen from U.S. Pat. No. 2,879,207, by Edward J. Poitras, for Filtration and Incubation Unit, issued Mar. 24, 1959 to Millipore Filter Corporation.

SUMMARY OF THE INVENTION

It is general object of this invention to overcome the disadvantages and to meet the needs mentioned in the above Information Disclosure Statement and in other parts hereof.

It is a germane object of the invention to provide a perfect air delivery monitoring system.

It is a related object of this invention to provide methods and apparatus for regularly monitoring an air delivery system including an air duct for contaminants.

It is also an object of this invention to improve ultimately the living environment inside buildings and other structures.

Other objects will become apparent in the further course of this disclosure.

From a first aspect thereof, the subject invention resides in a method of monitoring an air delivery system including an air duct for contaminants, comprising in combination the steps of providing an aperture in a wall of the air duct, covering that aperture with an insert having a bore, providing that insert with a filter element accessible from outside of the air duct, permitting air with contaminants to escape from the air duct through said bore, and trapping such contaminants with the filter element for subsequent laboratory analysis.

From a related aspect thereof, the invention resides also in apparatus for monitoring an air delivery system including an air duct for contaminants, such air duct having an aperture in a wall thereof, and, more specifically, resides in the improvement comprising, in combination, an air duct insert having a bore and covering said aperture, and a filter element in communication with that bore in a portion of the air duct insert accessible from outside of that air duct.

The invention also resides in apparatus comprising, in combination, an apertured filter element housing, a cylindrical air duct insert for said circular aperture in the air duct, a receptacle for that apertured filter element housing integral with the insert, an air conduit through that insert to that receptacle, and a mounting flange around the insert.

BRIEF DESCRIPTION OF THE DRAWINGS

The subject invention and its various aspects and objects will become readily apparent from the following detailed description of preferred embodiments thereof, illustrated by way of example in the accompanying drawings, in which like reference numerals designate like or equivalent parts, and in which.

DESCRIPTION OF PREFERRED EMBODIMENTS

Figure 1:
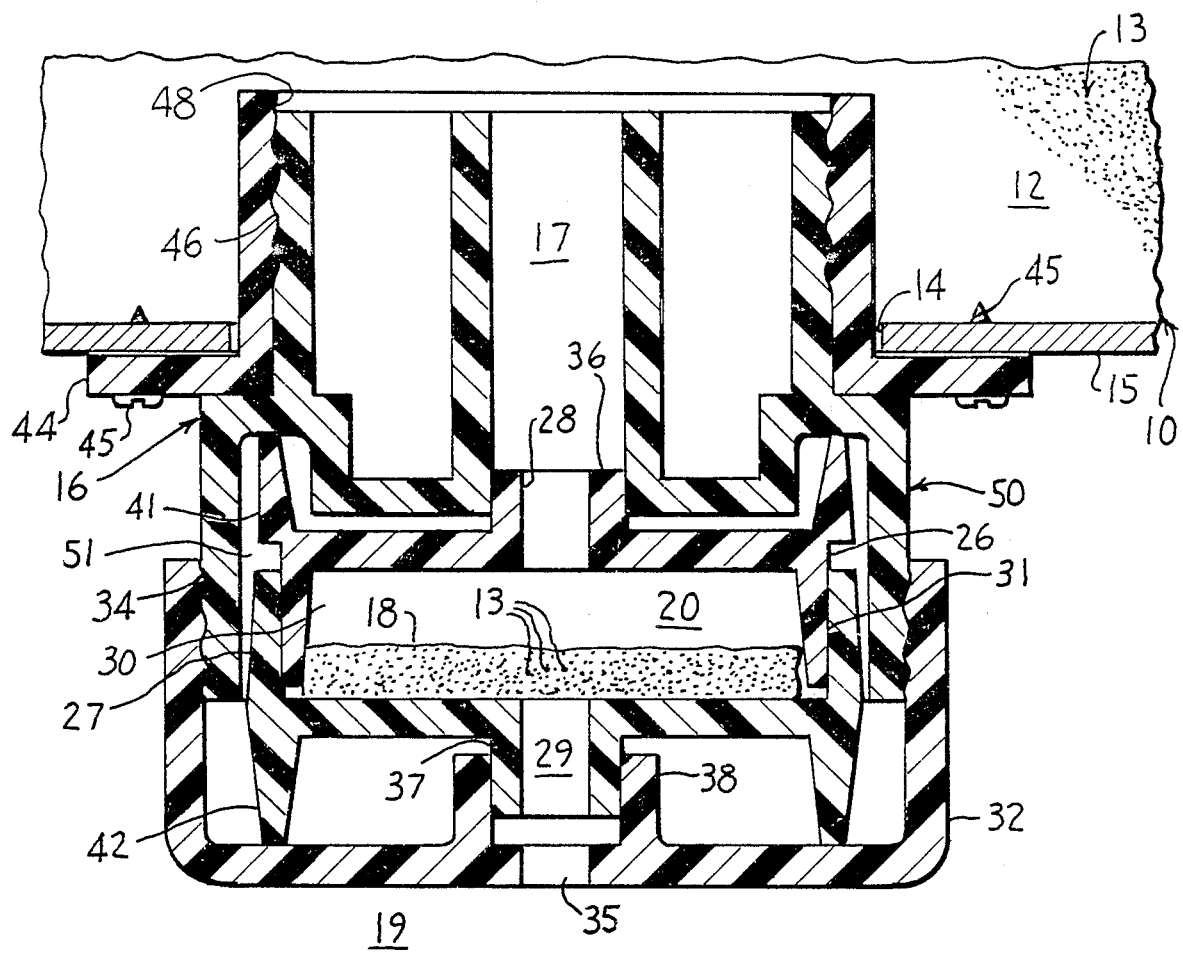
FIG. 1 is a section through a monitoring apparatus according to a preferred embodiment of the subject invention, as installed at an air duct of which a fraction has been shown.

The subject invention alleviates the above mentioned problems and avoids underlying disadvantages by constantly monitoring an air delivery system 10 including an air duct 12 for contaminants 13. To this end, an aperture 14 is provided in a wall 15 of the air duct. That aperture is covered with an insert 16 having a bore 17, which may be a longitudinal or axial bore communicating with the inside of the duct 12.

The insert 16 is provided with a filter element 18 accessible from an outside 19 of the air duct.

Air with contaminants 13 is permitted to escape from the air duct 12 through the bore 17 and such contaminants are trapped with the filter element 18 for subsequent laboratory analysis.

According to the illustrated embodiment of the invention, the filter element 18 is encapsulated in an apertured filter element housing 20, and such apertured filter element housing is mounted in the insert 16 in communication with the bore 17. Such filter element housing is opened or openable for a removal of the filter element 18 for laboratory analysis.

Figure 2:
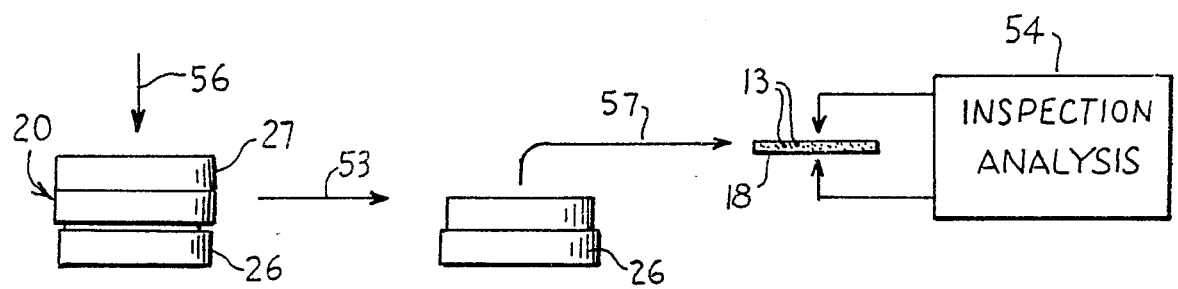
FIG. 2 is a flowsheet showing a removed filter element housing and a removed filter element on a reduced scale, as well as the transportation and processing thereof, and the inspection and analyses of filter element contaminants.

In practice, the apertured filter element housing 20 containing the filter element 18 is removed from the insert 16. A contaminated or used filter element may thus be carried, transported or sent to the lab, such as indicated by an arrow 53 in FIG. 2, where the housing 20 is opened for a removal of that filter element 18 for laboratory analysis, such as symbolically indicated by the block 54.

According to a preferred embodiment of the invention, the filter element 18 is encapsulated in an apertured filter element housing having mating housing parts or halves 21 and 22, and such apertured filter element housing is mounted in the insert 16 in communication with the bore 17, such as through a first filter element housing bore or inlet 28 in the first housing half 26.

A second filter element housing bore or inlet 29 enables flow of air from the duct 12 through the filter element 18 via bores 17, 28 and 29 for an entrainment of contaminants 13 in the filter element.

The housing parts or halves 26 and 27 may be interconnected by a manually releasable press fit 31, by mating threads (now shown), or in another suitable manner. After the apertured filter element housing 20 containing the filter element 18 has been removed from the insert 16, such as indicated by the arrow 56 in FIG. 2, the housing halves 26 and 27 are removed from each other for a removal of the contaminated filter element 18, such as indicated by the arrow 57 in FIG. 2, for laboratory analysis, such as symbolically indicated by the block 54.

According to the illustrated embodiment of the invention, an apertured cover 32 is provided for the insert 16, and the filter element housing is releasably retained with that cover in that insert.

The cover 32 may be threaded to the insert 16, such as at 34 and may have a bore or aperture 35 in communication with the filter element housing outlet 29. In practice, the bores or apertures 17, 28, 29, and 35 may be multiplied or staggered as desired or as necessary to assume optimum use of the filter element 18. However, air under pressure leaving the inlet 28 expands in the chamber 30 of the filter element housing, whereby the filter element 18 is covered by air for optimum entrainment of contaminants 13.

A circumvention of the filter element 18 by the contaminated air flowing from the duct 12 into the insert 16 is reliably avoided. For instance, the filter element housing 20, housing half 26, or inlet 28 is provided with a nipple 36 matching with the bore 17 for tightness and stability. The housing half 27 and the cover 32 have interacting or matching nipples 37 and 38 at air outlets 29 and 35.

The illustrated filter element housing halves 26 and 27 have shoulder portions 41 and 42 abutting respectively the insert 16 and the cover 32 at insides thereof for mounting stability of the filter element housing in the closed insert 16.

Shoulder portion 41 and also shoulder portion 42 may be circular or circularly in engagement with the insert inside and with the cover inside, respectively, for further air tightness around the filter element housing 20.

A flange 44 may be provided for the insert, and such insert 16 may be attached with such flange to the air duct wall 15 around the aperture 14. Sheet metal screws 45 or other suitable fasteners may be used for this purpose. The insert 16 may be threaded into the flange 44, such as shown at 46. In this manner, the bore of the flange may provide an inspection hole 48 or access for a duct cleaning tool.

In structural terms, the invention resides in apparatus 50 for monitoring an air delivery system 10 including an air duct 12 for contaminants 13, comprising the combination of an air duct insert 16 having a bore such as at 17 and covering an aperture 14 in an air duct wall 15, and a filter element 18 in communication with that bore in a portion 51 of the air duct insert 16 accessible from an outside 19 of the air duct.

A preferred embodiment of the invention includes an apertured cover 32 for the insert 16, with the filter element 18 releasably retained between that cover and the insert 16.

If the filter element 18 is encapsulated in an apertured filter element housing 20 according to an embodiment of the invention, then that filter element housing is releasably retained between the cover 32 and the insert 16, such as in a chamber 51 in the insert 16 or formed jointly by that insert and its cover 32.

The illustrated embodiment includes a mounting flange 44 around the insert 16, as already mentioned above.

The illustrated preferred embodiment of the invention presents an apparatus 50 for monitoring an air delivery system 10 including an air duct 12 for contaminants 13, comprising, in combination, an apertured filter element housing 20, a cylindrical air duct insert 16 for a circular aperture 14 in an air duct wall 15, a receptacle 51 for the apertured filter element housing integral with the insert 16, an air conduit 17 through that insert to that receptacle, and a mounting flange 44 around the insert 16. Within the scope of the invention, that flange may be integral with the insert. However, it is presently preferred that insert and flange be detachable from each other whereby the insert 16 can be conveniently removed from the flange 44 for inspection of the inside of the duct 12 and/or for a cleaning thereof.

An apertured cover 32 for the receptacle 51 may, for example, be threaded on the insert 16, and the filter element housing 20 may again comprise two apertured housing halves 41 and 42.

The parts of the apparatus 50 may be molded or manufactured of any suitable material. By way of example, plastics are suitable for this purpose. Reference in this may in this respect be had to the above mentioned U.S. Pat. No. 2,879,207.

In this respect, and in general, a bacteria or microorganism analysis may be effected at 54 to determine the microbiological content of the removed filter element. That filter element may also be subjected to a microscopic inspection and to an inspection or analysis for asbestos, fiberglass, rust and other particulate content. The technology to do all that exists, but the subject invention has put it together for air delivery system monitoring.

In this or any other manner within the scope of the subject invention, professionals concerned with an enhancement and maintenance of indoor quality of life not only are provided with an excellent and continuous management tool, but maintenance contractors and building owners alike are provided with honest assessments and appraisals for and of their works and of their systems as well.

The subject extensive disclosure will render apparent or suggest to those skilled in the art various modifications and variations within the spirit and scope of the subject invention and equivalents thereof.

I claim:

1. In a method of monitoring an air delivery system including an air duct for contaminants, the improvement comprising in combination the steps of:
   providing an aperture in a wall of said air duct;
   covering said aperture with an insert having a bore;
   providing said insert with a filter element accessible from outside of said air duct;
   permitting air with contaminants to escape from said air duct through said bore; and
   trapping said contaminants with said filter element for subsequent laboratory analysis.

2. A method as in claim 1, including the steps of:
   providing a flange for said insert; and
   attaching said insert with said flange to said wall around said aperture.

3. A method as in claim 1, including the steps of:
   encapsulating said filter element in an apertured filter element housing; and
   mounting said apertured filter element housing in said insert in communication with said bore.

4. A method as in claim 3, including the step of:
   opening said housing for a removal of said filter element for laboratory analysis.

5. A method as in claim 2, including the steps of:
   removing said apertured filter element housing containing said filter element from said insert; and
   opening said housing for a removal of said filter element for laboratory analysis.

6. A method as in claim 3, including the steps of:
   providing an apertured cover for said insert; and
   releasably retaining said filter element housing with said cover in said insert.

7. A method as in claim 1, including the steps of:
   encapsulating said filter element in an apertured filter element housing having mating housing halves; and
   mounting said apertured filter element housing in said insert in communication with said bore.

8. A method as in claim 7, including the steps of:
   removing said apertured filter element housing containing said filter element from said insert; and
   removing said housing halves from each other for a removal of said filter element for laboratory analysis.

9. A method as in claim 7, including the steps of:
   providing an apertured cover for said insert; and
   releasably retaining said filter element housing with said cover in said insert.

10. In apparatus for monitoring an air delivery system including an air duct for contaminants, said air duct having an aperture in a wall thereof, the improvement comprising in combination:
    an air duct insert having a bore and covering said aperture; and
    a filter element in communication with said bore in a portion of said air duct insert accessible from outside of said air duct.

11. Apparatus as in claim 10, including:
    an apertured cover for said insert;
    said filter element releasably retained between said cover and said insert.

12. Apparatus as in claim 10, including:
    an apertured filter element housing encapsulating said filter element in said insert in communication with said bore.

13. Apparatus as in claim 12, including:
    an apertured cover for said insert;
    said filter element housing releasably retained between said cover and said insert.

14. Apparatus as in claim 10, including:
    a mounting flange around said insert.

15. Apparatus as in claim 14, including:
    an apertured cover for said insert;
    said filter element releasably retained between said cover and said insert.

16. Apparatus as in claim 14, including:
    an apertured filter element housing encapsulating said filter element in said insert in communication with said bore.

17. Apparatus as in claim 16, including:
    an apertured cover for said insert;
    said filter element housing releasably retained between said cover and said insert.

18. In apparatus for monitoring an air delivery system including an air duct for contaminants, said air duct having a circular aperture in a wall thereof, the improvement comprising in combination:
    an apertured filter element housing;
    a cylindrical air duct insert for said circular aperture;
    a receptacle for said apertured filter element housing integral with said insert;
    an air conduit through said insert to said receptacle; and
    a mounting flange around said insert.

19. Apparatus as in claim 18, including:
    an apertured cover for said receptacle.

20. Apparatus as in claim 18, wherein:
    said filter element housing comprises two apertured housing halves.

* * * * *